United States Patent [19]

Carney et al.

[11] Patent Number: 4,859,699

[45] Date of Patent: Aug. 22, 1989

[54] SUBSTITUTED N-BENZOYL-N'-THIENYLUREAS

[75] Inventors: Robert L. Carney, Palo Alto; Alfred S. T. Lui, Redwood City, both of Calif.; Fred Kuhnen, Weil, Fed. Rep. of Germany; John M. Gruber, Menlo Park, Calif.

[73] Assignee: Sandoz Ltd., Basel, Switzerland

[21] Appl. No.: 316,253

[22] Filed: Feb. 23, 1989

Related U.S. Application Data

[63] Continuation of Ser. No. 211,515, Aug. 17, 1988, abandoned, which is a continuation-in-part of Ser. No. 167,595, Mar. 4, 1988, abandoned, which is a continuation-in-part of Ser. No. 75,504, Jul. 20, 1987, abandoned.

[51] Int. Cl.$^4$ .................. A01N 43/02; C07D 333/36; C07D 333/38; C07D 333/42
[52] U.S. Cl. .................... 514/447; 514/445; 514/337; 549/61; 549/63; 549/69; 546/284
[58] Field of Search ........... 514/445, 447, 336; 549/61, 63, 69; 546/284

[56] References Cited

U.S. PATENT DOCUMENTS

| | | | |
|---|---|---|---|
| 3,335,142 | 8/1967 | Hardy et al. | 549/69 |
| 3,828,001 | 8/1974 | Broad et al. | 549/69 |
| 3,872,106 | 3/1975 | Koch | 549/69 |
| 4,517,316 | 10/1986 | Plummer. | |
| 4,529,819 | 7/1985 | Clifford et al. . | |
| 4,599,356 | 8/1986 | Lange et al. . | |

FOREIGN PATENT DOCUMENTS

72438 2/1983 European Pat. Off. .
455015 12/1974 U.S.S.R. .

*Primary Examiner*—Alan Siegel
*Attorney, Agent, or Firm*—Jacqueline S. Larson

[57] ABSTRACT

Substituted N-benzoyl-N'-thienylureas, processes for making these compounds, intermediates therefor and the use of the compounds for the control of pests, and in particular for the control of insects and acarids.

20 Claims, No Drawings

SUBSTITUTED N-BENZOYL-N'-THIENYLUREAS

This is a continuation of Ser. No. 211,515, filed on Aug. 17, 1988, now abandoned, which is a continuation-in-part of Ser. No. 167,595, filed on Mar. 4, 1988, now abandoned, which is a continuation-in-part of Ser. No. 075,504, filed on July 20, 1987, now abandoned, which are incorporated herein by reference.

The present inventin relates to a substituted N-benzoylN'-thienylureas, to processes for producing these compounds, to intermediates therefor and to the use of the compounds for the control of pests, and in particular for the control of insects and acarids.

More particularly, the compounds of the present invention are represented by the following formula (A):

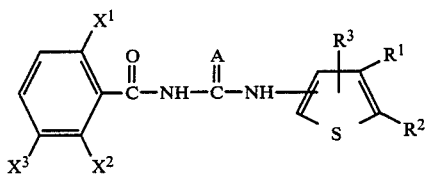

wherein,
A is oxygen or sulfur;
each of $X^1$, $X^2$ and $X^3$ is independently hydrogen, $C_{1-8}$alkyl or halogen;
each of $R^1$ and $R^2$ is independently hydrogen, halogen, cyano, unsubstituted or halogenated $C_{1-8}$alkyl, or the aryl group

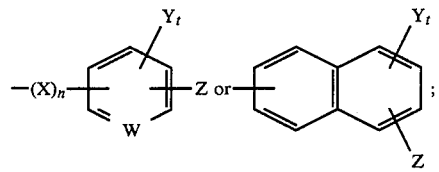

provided that when one of $R^1$ or $R^2$ is an arly group, the other of $R^1$ or $R^2$ is not an aryl group;
$R^3$ is hydrogen, halogen or COOR;
R is hydrogen or $C_{1-8}$alkyl;
n is zero or one;
t is one, two, three or four;
W is nitrogen or CH;
X is oxygen, sulfur or methylene;
Y is hydrogen, halogen, or unsubstituted or halogenated $C_{1-8}$alkyl; and
Z is halogen, unsubstituted or halogenated $C_{1-8}$alkyl, unsubstituted or halogenated $C_{1-8}$alkoxy, or unsubstituted or halogenated phenoxy;
and the agriculturally acceptable salts or metal complexes thereof.

In the description hereinafter and the appended claims, each of A, n, $R^1$-$R^3$, t, W, X-$X^3$, Y and Z is as defined above, unless otherwise specified.

Where any of the substituents $X^1$-$X^3$, $R^1$-$R^3$, Y and Z is or comprises halogen, such halogen is conveniently selected from bromo, chloro or fluoro.

Where any of $X^1$-$X^3$ is $C_{1-8}$alkyl, it is preferably of 1 to 4 carbon atoms and is more preferably of 1 or 2 carbons.

Where either of $R^1$ or $R^2$ is $C_{1-8}$alkyl, it is preferably of 1 to 4 carbon atoms and is more preferably of 1 or 2 carbons.

Where any of Y and Z is $C_{1-8}$alkyl, it is preferably of 1 to 4 carbon atoms and is more preferably of 1 or 2 carbons.

Where Z is $C_{1-8}$alkoxy, it is preferably of 1 to 4 carbon atoms.

The terms halogenated $C_{1-8}$alkyl, halogenated $C_{1-8}$alkoxy and halogenated phenoxy refer to $C_{1-8}$alkyl, $C_{1-8}$alkoxy and phenoxy, respectively, substituted by 1 to 8, preferably 1 to 6, and more preferably 1 to 3 halogens; such halogen is preferably chloro or fluoro and more preferably fluoro.

The term agriculturally acceptable salts or metal complexes of the acyl ureas refers to ammonium, sulfonium, phosphonium or metal ions such as, for example, tetraethylammonium, benzyltrimethylammonium, trimethylsulfonium, trimethylsulfoxonium, ethyltriphenylphosphonium, titanium(IV), zirconium(IV) or zinc(II).

In the practice of the present invention, A is preferably oxygen.

W is preferably CH.

$X^1$ is preferably halogen; such halogen is preferably chloro or fluoro.

$X^2$ is preferably hydrogen or halogen; such halogen is preferably fluoro.

$X^3$ is preferably hydrogen.

Each of $R^1$ and $R^2$ independently conveniently signifies hydrogen, $C_{1-4}$alkyl, halogenated $C_{1-4}$alkyl, halogen or the substituted phenyl group

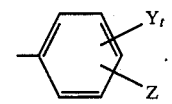

$R^1$ and $R^2$ are preferably hydrogen, methyl, $CF_3$, chloro or the substituted phenyl group; provided that when one of $R^1$ or $R^2$ is the substituted phenyl group, the other of $R^1$ or $R^2$ is other than substituted phenyl.

$R^3$ is preferably hydrogen, fluoro or chloro, more preferably hydrogen.

t is preferably one or two, more preferably one.

Y is preferably hydrogen or halogen; such halogen is preferably chloro or fluoro, more preferably chloro. Y is more preferably hydrogen.

Z is preferably unsubstituted or halogenated $C_{1-4}$alkyl, unsubstituted or halogenated $C_{1-4}$alkoxy or halogen, and is more preferably methyl, methoxy, $OCHF_2$, $OCF_3$, $CF_3$, bromo, chloro or fluoro.

The urea nitrogen atom is preferably bonded to the 2-position of the thiophene ring.

The compounds of the present invention of formula (A) are new substances which can be prepared by methods known in the art, such as those described in U.S. Patents 3,978,356 and 3,933,908 and in U.K. Application GB 2134518, for example. More particularly, they can be obtained by:

reacting a benzoyl isocyanate or isothiocyanate of formula (I)

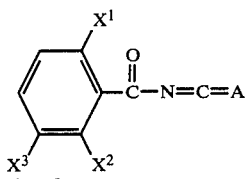

wherein $X^1$, $X^2$, $X^3$ and A are as defined above, with an aminothiophene of formula (II)

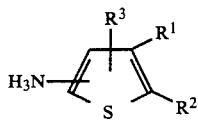

wherein $R^1$, $R^2$ and $R^3$ are as defined above, or the acid salt thereof.

The reaction of compounds of formula I with compounds of formula II may be effected under the conditions known for the preparation of N-benzoyl-N'-thienylureas from the corresponding isocyanates or isothiocyanates and aminothiophenes or acid salts of aminothiophenes.

The reaction is conveniently carried out in a solvent which is inert under the reaction conditions, e.g., methylene chloride, toluene or dimethylformamide. A suitable reaction temperature may vary from $-10°$ C. to the boiling point of the solvent used, and preferably is about room temperature or moderately above or below room temperature, e.g. between 15° and 40° C. The reaction is optionally carried out in the presence of an organic base, for example triethylamine.

The salts of the compounds of formula (A) may be prepared by reaction of the ammonium, sulfonium or phosphonium halide with the compound (A) in the presence of a base, such as potassium hydroxide, and a water-immiscible solvent, such as dichloromethane.

The metal complexes of the compounds of formula (A) may be prepared by reaction of the compound (A) with the metal alkoxide, such as titanium tetraisopropoxide, under vacuum at a temperature that permits removal of the alcohol product by distillation, typically 75° to 100°.

The compounds of formula (A) may be recovered from the reaction mixture in which they are formed by working up by established procedures.

The starting materials and reagents employed in the processes described above are either known or, in cases where they are novel, may be produced by methods analogous to the processes described herein or to known processes.

The compounds of the present invention of formula (A) are useful pest control agents, particularly for the control of insects, mites, ticks and helminths. These compounds can be effective control agents for insects of, for example, the orders Lepidoptera, Hemiptera, Homoptera, Coleoptera, Diptera, Orthoptera and Siphonaptera, and other insects, as well as for mites and ticks of the class Acari, including mites of the families Tetranychidae and Tarsonemidae and ticks of the families Argasidae and Ixodidae. The compounds can be applied to the pest or its locus in a pest-controlling amount, usually of the order of 0.0001 ug to 100 ug per insect, mite or tick, depending on the mode and conditions of application as well as on the pest involved.

These compounds may be useful anthelmintic agents against parasites of warm-blodded animals and of plants, such as, for example, intestinal and extraintestinal nematodes of the families Ascaridae and Trichostrongylidae and plant parasitic nematodes of the families Heteroderidae and Tylenchidae.

Additionally, compounds of formula (A) may possess a repellant and/or antifeedant action on terrestrial snails and slugs. The compounds may also be useful for control of arthropod endoparasites and ectoparasites of vertebrates, either by topical application or by oral administration to the host animal.

The compounds of the present invention may be used as an active ingredient in anti-fouling marine paints to prevent attachment of marine arthropods, such as barnacles.

In the use of the compounds of formula (A) for combatting pest, a compound of formula (A), or mixtures thereof, can conveniently be employed as pesticidal compositions in association with acceptable diluent(s) for application to the pest or its locus. Such compositions also form part of the present invention.

Suitable formulations contain from 0.01 to 99% by weight of active ingredient, from 0 to 20% of surfactant and from 1 to 99.9% of solid or liquid diluent(s). Higher ratios of surfactant to active ingredient are sometimes desirable and are achieved by incorporation into the formulation or by tank mixing. Application forms of a composition generally contain between 0.01 to 25% by weight of active ingredient. Lower or higher levels of active ingredient can, of course, be present depending on the intended use, the physical properties of the compound and the mode of application. Concentrate forms of a composition intended to be diluted before use generally contain between 2 and 90%, preferably between 5 and 81% by weight of active ingredients.

Useful formulations of the compounds of formula (A) include dusts, granules, suspension concentrates, emulsifiable concentrates, wettable powders, flowables and the like. They are obtained by conventional manner, e.g. by mixing a compound of formula (A) with the diluent(s) and optionally with other ingredients.

Alternatively, the compounds of formula (A) may be used in micro-encapsulated form.

The compounds of formula (A) can be combined with beta or gamma cyclodextrin to make a cyclodextrin inclusion complex for application to the pest or its locus.

Agriculturally acceptable additives may be employed in the pesticidal compositions to improve the performance of the active ingredient and to reduce foaming, caking and corrosion, for example, "Surfactant" as used herein means an agriculturally acceptable material which imparts emulsifiability, spreading, wetting, dispersibility or other surface-modifying properties. Examples of surfactants are sodium lignin sulfonate and lauryl sulfate.

"Diluent" as used herein means a liquid or solid agriculturally acceptable material used to dilute a concentrated material to a usable or desirable strength. For dusts or granules it can be e.g. talc, kaolin or diatomaceous earth, for liquid concentrate forms for example a hydrocarbon such as xylene or an alcohol such as isopropanol, and for liquid application forms for example water or diesel oil.

The compositions of this invention can also comprise other compounds having biological activity, e.g. compounds having similar or complementary pesticidal or insect growth regulating activity or compounds having antidotal, fungicidal, herbicidal or insect attractant activity.

The following examples are provided to illustrate the practice of the present invention. Temperature is given in degrees Celsius. RT means room temperature. Parts and percentages are by weight.

COMPOSITION EXAMPLES

Example A:

| Flowable | |
|---|---|
| Compound 1 | 26.00% |
| Morwet ® D425 (dispersant) | 5.20 |
| Vegum ® (thickener) | 0.38 |
| Surfynol ® TGE (antifoam) | 0.05 |
| Foamaster UDB (antifoam) | 0.05 |
| water | 61.52 |
| propylene glycol (antifreeze) | 6.60 |
| Kelzan ® (thickener) | 0.20 |

Morwet is sodium sulfonate of naphthalene formaldehyde condensate.
Veegum is colloidal magnesium aluminum silicate.
Surfynol is acetylenic diol blend.
Foamaster is a silicone proprietary mixture.
Kelzan is xanthan gum.

Example B:

| Wettable Powder | |
|---|---|
| Compound 1 | 81.0% |
| kaolin | 14.8 |
| Marasperse ® N-22 (dispersant) | 4.0 |
| Aerosol ® OTB (wetting agent) | 0.2 |

Marasperse is sodium lignin sulfonate.
Aerosol is dioctyl ester of sodium sulfosuccinic acid.

PREPARATION OF FINAL UREAS

Example 1:

N-2,6-diflurobenzoyl-N'-[5-(4-chlorophenyl)4-methyl-2-thienyl]urea

To a solution of 2-amino-4-methyl-5-(4-chlorophenyl)thiophene HCl (0.45 g, 1.73 mmol) i 4 ml of dimethylformamide and 4 ml of methylene chloride is added 2,6-difluorobenzoylisocyanate (0.32 g, 1.73 mmol), followed by triethylamine (0.23 g, 0.3 ml, 2.25 mmol). The mixture is stirred overnight at RT, after which water is added and the solvent is removed. The residue is filtered, and the solid is washed with 50% hexane/methylene chloride to give N-2,6-difluorobenzoyl-N'-[5-(4-chlorophenyl)-4-methyl-2-thienyl]urea (compound 1 under Table A).

Example 2:

N-2,6-difluorobenzoyl-N'-[5,(4-trifluoromethoxyphenyl)-4-methyl-2-thienyl]urea

To a solution of 2-amino-4-methyl-5-(4-trifluoromethoxyphenyl)thiophene trifluoroacetic acid salt (1.88 mmol) in 30 ml of methylene chloride is added, with cooling, triethylamine (3.75 mmol), followed by 2,6-difluorobenzoylisocyanate (1.88 mmol). The mixture is worked up as in Example 1 to give the corresponding urea (compound 41, Table A).

Example 3:

Following the procedures of Example 1 or Example 2, each of the final compounds under Table A and Table B is prepared from the corresponding thiophene or thiophene acid salt and benzoyl isocyanate or isothiocyanate intermediates.

Example 4:

3-Amino-5-(4-chlorophenyl-thiophene is reacted with each of 2,6-difluorobenzoyl isocyanate and 2-chlorobenzoyl isocyanate, following the procedure of Example 1, to give, respectively,
N-2,6-difluorobenzoyl-N'-[5-(4-chlorophenyl)-3-thienyl]urea, (compound 32 under Table C) and
N-2-chlorobenzoyl-N'-[5-(4-chlorophenyl)-3-thienyl]urea, (compound 33 under Table C).

In the same manner, each of the final compounds under Table C is prepared from the corresponding thiophene or thiophene acid salt and benzoyl isocyanate or isothiocyante intermediates.

TABLE A

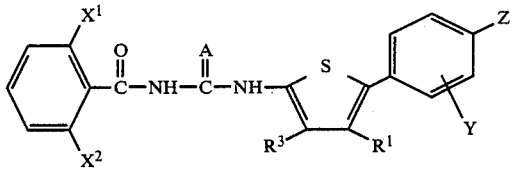

| Cpd | X¹ | X² | A | R¹ | R³ | Y | Z | m.p. (°C.) |
|---|---|---|---|---|---|---|---|---|
| 1 | F | F | O | CH₃ | H | H | Cl | 203–205 |
| 2 | Cl | H | O | CH₃ | H | H | Cl | 188–190 |
| 3 | F | H | O | CH₃ | H | H | Cl | 186–188 |
| 4 | F | F | O | CF₃ | H | H | Cl | 208–209 |
| 5 | F | F | O | H | H | H | Cl | 231–232 |
| 6 | Cl | H | O | H | H | H | Cl | 216–218 |
| 7 | F | F | O | H | H | 3-Cl | Cl | 211–213 |
| 8 | Cl | H | O | H | H | 3-Cl | Cl | 201–202 |
| 9 | F | F | O | CH₃ | H | H | F | 188–190 |

TABLE A-continued

Structure: 2,6-disubstituted benzoyl-NH-C(A)-NH-thiophene (with S, R¹, R³ on thiophene) linked to phenyl with Y, Z substituents

| Cpd | X¹ | X² | A | R¹ | R³ | Y | Z | m.p. (°C.) |
|---|---|---|---|---|---|---|---|---|
| 10 | Cl | H | O | CH₃ | H | H | F | 175–177 |
| 11 | F | F | O | CH₃ | H | H | Br | 207–209 |
| 12 | Cl | H | O | CH₃ | H | H | Br | 197–199 |
| 13 | F | F | O | CH₃ | H | H | CF₃ | 228–229 |
| 14 | Cl | H | O | CH₃ | H | H | CF₃ | 202–204 |
| 15 | F | F | O | CH₃ | H | 3-Cl | Cl | 181–183 |
| 16 | Cl | H | O | CH₃ | H | 3-Cl | Cl | 195–197 |
| 17 | F | F | O | CH₃ | H | H | H | 203–205 |
| 18 | Cl | H | O | CH₃ | H | H | H | 207–208 |
| 19 | F | F | O | Cl | H | H | Cl | 211–213 |
| 20 | Cl | H | O | Cl | H | H | Cl | 201–202 |
| 21 | Cl | H | O | H | Cl | H | Cl | 243–245 |
| 22 | Cl | H | O | Cl | Cl | H | Cl | oil |
| 23 | Cl | H | O | CH₃ | COOH | H | Cl | 235 |
| 24 | F | F | O | CH₃ | COOH | H | Cl | 240–241 |
| 36 | F | F | S | CH₃ | H | H | Cl | 180.5–181.5 |
| 37 | F | F | O | CH₃ | COOCH₃ | H | Cl | 275–278 |
| 38 | Cl | H | O | CH₃ | COOCH₃ | H | Cl | 245–246 |
| 39 | F | F | O | CH₃ | COOC(CH₃)₃ | H | Cl | 207–208 |
| 40 | Cl | F | O | CH₃ | COOC(CH₃)₃ | H | Cl | 243–244 |
| 41 | F | F | O | CH₃ | H | H | OCF₃ | 201–202 |
| 42 | F | F | O | CH₃ | H | 2-Cl | CF₃ | 199–200 |
| 43 | F | F | O | CH₃ | H | 2-F | Cl | 190–191 |
| 44 | F | F | O | CH₃ | H | 3,5-diCl | H | 239–240 |
| 45 | F | F | O | CH₃ | H | 2-Cl,5-CF₃ | H | 171–172 |
| 50 | F | F | O | CH₃ | H | H | —O—(4-Cl-phenyl) | 202–203 |
| 51 | F | F | O | CH₃ | H | 2-Cl | OCF₃ | 171–172 |

TABLE B

Structure: 2,6-disubstituted benzoyl-NH-C(A)-NH-thiophene with R¹ and R² substituents

| Cpd | X¹ | X² | A | R¹ | R² | m.p. (°C.) |
|---|---|---|---|---|---|---|
| 25 | F | F | O | Cl | Cl | 215–219 |
| 26 | Cl | H | O | Cl | Cl | 225–227 |
| 27 | F | F | O | 4-Cl-phenyl | H | 247–249 |
| 28 | Cl | H | O | 4-Cl-phenyl | H | 217–219 |
| 29 | F | F | O | 4-Cl-phenyl | CH₃ | 230–231 |
| 30 | Cl | H | O | 4-Cl-phenyl | CH₃ | — |
| 31 | F | F | O | —CH₂—(4-Cl-phenyl) | H | 194–196 |
| 52 | F | F | O | —CH₂—(3-Cl,4-OCF₃-phenyl) | H | 184–186 |

TABLE C

![structure: X1,X2-substituted benzoyl-NH-C(A)-NH-thiophene with R1,R2,R3]

| Cpd | X¹ | X² | A | R¹ | R² | R³ | m.p. (°C.) |
|---|---|---|---|---|---|---|---|
| 32 | F | F | O | H | —⟨phenyl⟩—Cl | H | 235–237 |
| 33 | Cl | H | O | H | —⟨phenyl⟩—Cl | H | 214–216 |
| 34 | F | F | O | H | —⟨phenyl⟩—Cl | Cl | 243–245 |
| 35 | Cl | H | O | H | —⟨phenyl⟩—Cl | Cl | 220 |
| 46 | F | H | O | H | $CF_3$ | H | 134 |
| 47 | Cl | H | O | H | $CF_3$ | H | 177 |
| 48 | F | F | O | H | $CF_3$ | H | 180–181 |
| 49 | Cl | Cl | O | H | $CF_3$ | H | 182–184 |

BIOASSAY EXAMPLES

Example 5:

Mosquito Assay

Fifty microliters of compound at the test concentration is mixed into 50 ml of tap water in plastic tumblers (3 tumblers per concentration). Ten later fourth instar yellow fever mosquito (*Aedes aegypti*) larvae are then place into each tumbler. A few drops of liver powder suspension are added as a food source. The tumblers are covered and the larvae are allowed to develop, at 28°, to adult emergence, usually 6 days. The assay is scored for the $ED_{50}$, which is the dose at which 50% of the insects are affected (e.g., larval mortality, pupal mortality, failure of the adults to emerge completely). Results of selected compounds are shown under Table D.

Example 6:

Tobacco Budworm Assay

Third instar larvae (less than 24 hr. post-molt) of tobacco budworm (Heliothis virescens) are treated topically on the dorsal abdomen with 1 ul of compound at the test concentration. Larvae are then placed on artificial diet in individual cells of a plastic grid contained in a covered container (placing larvae in individual cells prevents cannibalism), and held at 27° through two molts to the fifth instar, usually 8 days. The assay is scored for the $ED_{50}$, which is the dose at which 50% of the insects are affected (e.g., larval mortality, growth inhibition, cuticular abnormalities). Results of selected compounds are shown in Table D.

Example 7:

Beet Armyworm Assay

Fourth instar larvae (less than 24 hr. post-molt) are treated topically on the dorsal abdomen with 1 ul of compound at the test concentration. The larvae are then placed on artificial diet in a covered container and held at 27° through two molts to pupation, usually 10 days. The assay is scored for the $ED_{50}$, which is the dose at which 50% of the insects are affected (e.g., larval mortality, growth inhibition, cuticular abnormalities). Results of selected compounds are shown in Table D.

TABLE D

| | Bioassay Results $ED_{50}$ | | |
|---|---|---|---|
| Cpd | Aedes (ppm) | Heliothis (ug/insect) | Spodoptera (ug/insect) |
| 1 | 0.0060 | 0.043 | 0.0077 |
| 4 | 0.00039 | 0.030 | 0.0072 |
| 5 | 0.0032 | 0.18 | 0.017 |
| 9 | 0.0046 | 0.12 | 0.039 |
| 10 | 0.010 | 0.099 | 0.046 |
| 11 | 0.0038 | 0.040 | 0.0066 |
| 12 | >0.10 | >1.00 | 0.013 |
| 13 | 0.0026 | 0.090 | 0.0039 |
| 14 | 0.0025 | 0.93 | 0.0044 |
| 15 | 0.0046 | 0.032 | 0.013 |
| 16 | 0.039 | 0.32 | 0.086 |
| 17 | 0.0068 | >1.0 | 0.11 |
| 19 | 0.0029 | 0.049 | 0.014 |
| 20 | 0.0026 | 4.5 | 0.079 |
| 25 | 0.0038 | 0.26 | 0.25 |
| 26 | 0.0031 | 1.0 | 0.45 |
| 31 | 0.0038 | 0.37 | 0.073 |
| 36 | 0.031 | 0.67 | 0.11 |
| 48 | 0.023 | >1.0 | 0.11 |
| 49 | 0.039 | >1.0 | 0.29 |
| 51 | — | <1.0 | 0.0037 |

The starting materials of formulas I and II hereinn are known or, in cases where they are novel, may be produced by methods analogous to known methods or by methods described herein. Thus, the compounds of formula I can be synthesized by methods described in U.S. Patent 3,933,908, for example by (a) treating the corresponding benzamide with oxalyl chloride in the presence of a solvent such as chlorinated hydrocarbon, as described in J. Agr. Food Chem. 21(3):348 (1973); or by (b) reacting the corresponding benzoyl chloride with ammonium thiocyanate.

The aminothiophene derivatives of formula II can be prepared by several methods such as the following, for example: (a) By the reduction or catalytic hydrogenation of the corresponding nitro compounds of formula III.

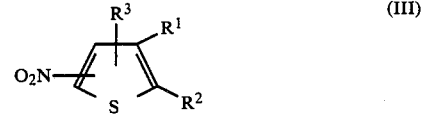

(III)

(b) Where the compounds are 3-aminothiophenes, by the dehydration of the corresponding compounds of formula IV.

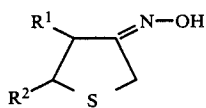

(c) Where the compounds are 2-aminothiophenes and $R^1$ and $R^3$ are hydrogen, by the reaction of a compound of formula V with hydrogen sulfide and HCl.

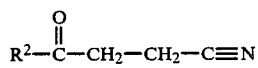

(d) Where the compounds are 2-aminothiophenes, by the following reaction:

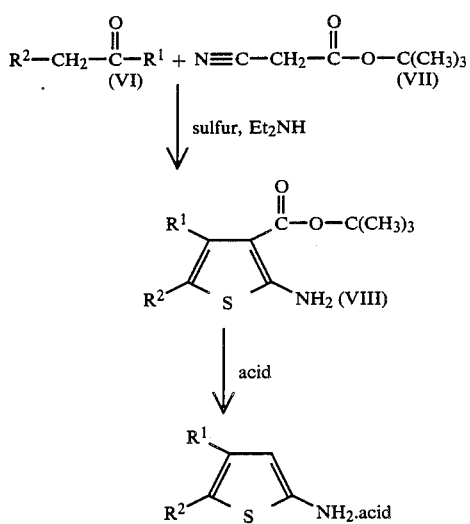

PREPARATION OF INTERMEDIATE COMPOUNDS

The following examples are presented to illustrate representative methods of preparing the intermediate aminothiophene hydrochloric acid or trifluoroacetic acid salts.

Example 8:

2-Amino-4-methyl-5-(4-chlorophenyl)thiophene HCl

To a mixture of 4-chlorophenylacetone (5.0 g, 29.7 mmol), t-butylcyanoacetate (4.19 g, 29.7 mmol) and sulfur (0.95 g, 29.7 mmol) in 12 ml of ethanol is added diethylamine (4 ml), and the mixture is heated to 60° for 4 hours. The reaction mixture is then diluted with water and extracted with ethyl acetate. The combined organic layers are washed with water and with brine and dried, and the crude product is purified to give 2-amino-3-(t-butoxycarbonyl)-4-methyl-5-(4-chlorophenyl)thiophene.

The above thiophene (2.0 g) in 10 ml of 6M HCl is heated at 80° for 33 hours. Ethanol is added, and the solvent and water are then removed. Ether is added to the residue, the suspension is filtered and the final solid is rinsed with ether to give 2-amino-4-methyl-5-(4-chlorophenyl)thiophene hydrochloric acid salt.

Example 9:

2-Amino-4-trifluoromethyl-5-(4-chlorophenyl)thiophene trifluoroacetic acid salt

Following the procedure of Example 8, 2-amino-3-(t-butoxycarbonyl)-4-trifluoromethyl-5-(4-chlorophenyl)-thiophene is prepared from 1,1,1-trifluoro-3-(4-chlorophenyl)acetone (2.60 g), t-butylcyanoacetate (1.65 g) and sulfur (0.37 g).

The above thiophene (0.30 g) is treated with trifluoroacetic acid (TFA) (3 ml), and the mixture is stirred at RT overnight. The excess TFA is evaporated off to give 2-amino-4-trifluoromethyl-5-(4-chlorophenyl)thiophene trifluoroacetic acid salt.

Example 10:

2-Amino-4-(4-chlorophenyl)-5-methylthiophene trifluoroacetic acid salt

A stirred mixture of 4-chloropropiophenone (4.0 g, 24.0 mmol) and t-butylcyanoacetate (4.0 g, 4.1 ml, 28.0 mmol) in 40 ml of toluene and 2 ml of acetic acid is heated under reflux. Ammonium acetate (1.82 g, 24.0 mmol) is added in portions over 72 hours as the water formed in the reaction is removed azeotropically. The reaction is then cooled, stripped of solvents, and the resulting clear oil mixture purified by chromatography to yield (E,Z)-t-butyl-3-(4-chlorophenyl)-2-cyano-2-pentanoate.

A mixture of the above pentanoate (1.5 g, 5.1 mmol), sulfur (0.18 g, 5.7 mmol), ethanol (15 ml) and diethylamine (7 ml) is stirred at 40° C. for 3 hours. The reaction mixture is taken up in ether and washed with water and brine, then dried over sodium sulfate and the solvents stripped off. The product is purified by chromatography to yield 2-amino-3-(t-butoxycarbonyl)-4-)4-chlorophenyl)-5-methylthiophene.

The above thiophene (0.70 g) is stirred for 20 hours in 4 ml of trifluoroacetic acid, after which the trifluoroacetic acid is evaporated off using a toluene azeotrope to yield 2-amino-4-(4-chlorophenyl)-5-methylthiophene trifluoroacetic acid salt.

Example 11:

2-Amino-5-(4-chlorophenyl)thiophene HCl

To a mixture of freshly ground sodium cyanide (0.75 g, 15.0 mmol) in dimethylformamide (DMF) is added, over 30 min., 4-chlorobenzaldehyde (21.0 g, 150.0 mmol) in DMF. 30 Minutes after the addition is completed, acrylonitrile (5.96 g, 7.4 ml, 112.5 mmol) is added over a period of 1 hour. The mixture is stirred at RT for 3 hours, after which acetic acid (0.99 g, 0.94 ml, 16.5 mmol) is added. After 5 min., the reaction mixture is poured into water and extracted with chloroform. The combined chloroform layers are washed with water and with brine, dried and stripped of solvent. The residue is recrystallized and filtered to give 4-(4-chlorophenyl)-4-oxobutyronitrile.

HCl and $H_2S$ gas are bubbled through a solution of the above nitrile (7.70 g, 40.0 mmol) in 100 ml of methanol at 10°–20° for 7 hours. The suspension is then stirred at RT overnight. It is dried, filtered, washed with ether and dried with suction under an $N_2$ atmosphere to give 2-amino-5-(4-chlorophenyl)thiophene hydrochloric acid salt, a slightly purplish powder.

Example 12:

2-Amino-4,5-dichlorothiophene HCl

To a solution of 2-nitrothiophene (10.0 g, 77.5 mmol) in 60 ml of chloroform is added aluminum chloride (6.0 g, 45.0 mmol). The mixture is cooled to 10° and chlorine gas is bubbled through for 3 hours at 25°-30°. Nitrogen gas is then bubbled through the mixture for 10 min., after which the mixture is poured into ice water and extracted with chloroform. The combined chloroform layers are washed with water and with brine and dried to give 2-nitro-4,5-dichlorothiophene.

To a cooled solution of the above 4,5-dichlorothiophene (13.0 g, 66.0 mmol) are added acetic acid (78 ml) and acetic anhydride (78 ml), followed by iron powder (13.0 g) in portions over 30 min. at such rate that the mixture is kept at 5°-10°. The suspension is stirred at RT overnight, after which it is poured into water, acidified with conc. HCl and cooled in an ice bath for 6 hours. It is then filtered, and the solid is washed with water and dried, dissolved in ether and filtered. Charcoal is added to the filtrate, which is then filterded and stripped of solvent to give N-(4,5-dichloro-2-thienyl)acetamide, a solid.

HCl gas is bubbled through a solution of the above made (1.5 g) in 10 ml of methanol for 1 hour. The resulting suspension is stripped of solvent, and the residue is filtered and washed with ether to give 2-amino-4,5-dichlorothiophene hydrochloric acid salt.

Example 13:

2-Amino-4-chloro-5-(4-chlorophenyl)thiophene HCl

4-Chloroaniline (4.0 g, 31.4 mmol) is added to 4 ml of acetic acid and heated until all solid is dissolved. The solution is cooled to 5° and 5.2 ml of conc. HCl is added, followed by the dropwise addition of sodium nitrite (2.16 g, 31.4 mmol) in 32 ml of water. After addition is complete, the mixture is stirred at 5° for 1 hour. Thiophene (2.64 g, 2.5 ml, 31.4 mmol) in 25 ml of carbon tetrachloride is added to the mixture, followed by the dropwise addition of 25% aq. NaOH (ca. 6.8 ml). After 1 hour, the mixture is poured into water and extracted with chloroform, and the combined extracts are washed with brine, dried and stripped of solvent. The black residue is distilled at ca. 120° 0.35 mm to give 2-(4-chlorophenyl)thiophene, a yellow solid.

A solution of the above phenylthiophene (10.6 g, 54.0 mmol) in 100 ml of acetic anhydride is added dropwise to a solution of cupric nitrate (6.3 g, 27.0 mmol) in 100 ml of acetic anhydride at 10°-12°. The mixture is stirred at RT for 2 hours, then poured into ice water and extracted with ethyl acetate. The combined organic layers are washed with water and with brine, dried and stripped of solvent to give a dark brown solid which is purified to yield 2-nitro-5-(4-chlorophenyl)thiophene.

Chlorine gas is bubbled through a suspension of the above nitrothiophene (0.5 g) in 6 ml of acetic acid for 3.5 hours, after which the solvent is stripped off and the residue is purified to give 2-nitro-4-chloro-5-(4-chlorophenyl)thiophene.

Following the procedure of Example 12, 2-nitro-4-chloro-5-(4-chlorophenyl)thiophene (2.3 g) is reacted with acetic anhydride (14 ml) and iron powder (2.3 g) in acetic acid (14 ml), followed by reacton with HCl and methanol (30 ml) to give 2-amino-4-chloro-5-(4-chlorophenyl)thiophene hydrochloric acid salt.

Example 14:

3-Amino-5-(4-chlorophenyl)thiophene HCl

To a stirred mixture of mercaptoacetic acid (5.04 g, 3.8 ml, 54.7 mmol) and 4-chlorocinnamic acid (10.0 g, 54.7 mmol) in 20 ml of dioxane is added dropwise a solution of triethylamine (6.90 g, 9.53 ml, 68.0 mmol) in 20 ml of dioxane. The mixture is heated under reflux for 5 hours, then cooled and poured into ice, acidified with conc. sulfuric acid and extracted with ether. The combined ether extracts are washed with water and with brine, dried and stripped of the solvent. The residue is washed with chloroform to give 3-carboxymethylthio-3-(4-chlorophenyl)propionic acid, a yellow solid.

A mixture of the above propionic acid (12.75 g, 46.6 mmol), lithium carbonate (0.23 g) and acetic anhydride (35 ml) is heated under reflux overnight. The mixture is then poured into 100 g ice and 1.5 ml conc. sulfuric acid and stirred at under 25° for 2 hours. It is extracted with ether, and the ether extracts are stripped of solvent. The residue is taken up in ether and basified, then washed with brine, dried, stripped of solvent and purified to give 5-(4-chlorophenyl)-3-oxytetrahydrothiophene, a yellow solid.

A mixture of the above tetrahydrothiophene (5.70 g, 27.0 mmol), hydroxylamine HCl (2.81 g, 40.0 mmol) and barium carbonate (5.60 g) in 70 ml of ethanol is heated under reflux overnight. The solid is filtered and washed with 250 ml of hot ethanol. The filtrate is stripped of solvent, and the residue is diluted with ether and ethyl acetate, washed with water and with brine, dried and stripped of solvent to give 2-(4-chlorophenyl)-4-oxotetrahydrothiophene oxime.

Following the procedure of Example 12, the above oxime (6.14 g, 27.0 mmol) is reacted with HCl and methanol to give 3-amino-5-(4-chlorophenyl)thiophene hydrochloric acid salt.

Example 15:

2-Amino-4-methyl-5-(4-trifluoromethoxyphenyl)thiophene trifluoroacetic acid salt.

A solution of 4-trifluoromethoxy aniline (5.3 g, 30 mmol) in fluoboric acid (48%, 20 ml) and water (20 ml) is chilled with an ice bath and treated with sodium nitrate (30 mmol) in 10 ml of water. After 15 min., the resulting slurry is filtered. This solid is slurried with ether and dried in vacuo.

To a slurry of this diazonium salt (2.5 g, 9.1 mmol) in isopropanol acetate (10 ml) is added KOAc (1.5 g, 15 mmol) with cooling from a water bath. After 20 min., the reaction mixture is partitioned between ether/hexane and water. The organic solution is washed with water (2X) and aq. NaHCO$_3$ and dried (Na$_2$SO$_4$). Concentration and flash chromatography gives 4-trifluoromethoxyphenyl acetone.

A solution of the above ketone (1.2 g, 5.5 mmol), t-butylcyanoacetate (1.4 g, 10 mmol), amyl amine (5 drops) and acetic acid (8 drops) in toluene (10 ml) is heated to reflux with removal of water. After 3 hr., an additional quantity of amyl amine (3 drops) and acetic acid (3 drops) are charged. Reflux is continued for 3 hr. The reaction mixture is cooled and partitioned between ether/hexane and water. The organic phase is washed with dilute HCl and 5% in vacuo. Flash chromatography gives the condensation product as a mixture of E and Z isomers.

This product (1.3 g, 3.9 mmol) is dissolved in 10 ml of absolute ethanol and treated with sulfur (0.16 g, 5 mmol) and diethylamine (0.35 g, 5 mmol). The mixture is stirred at RT for 2 hr. and then heated to 50° C. for 1 hr. The reaction mixture is cooled and worked up as in the previous reaction. Flash chromatography followed by crystallization from hexane gives 2-amino-3-(t-butoxycarbonyl)-4-methyl-5-(4-trifluoromethoxyphenyl)thiophene.

The above thiophene (0.7 g) in 6 ml of trifluoroacetic acid is heated to 60° C. for 3 hr., cooled, diluted with toluene and concentrated in vacuo. The resulting oil is diluted and concentated twice more to afford 2-amino-4-methyl-5-(4-trifluoromethyloxyphenyl)thiophene trifluoroacetic acid salt.

What is claimed is:

1. A compound of the following formula (A):

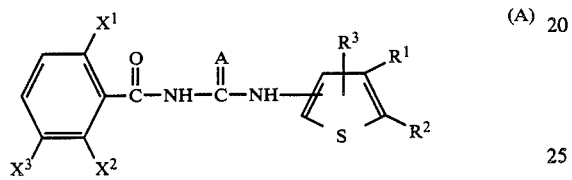

wherein,
A is oxygen or sulfur;
each of $X^1$, $X^2$ and $X^3$ is independently hydrogen, $C_{1-8}$alkyl or halogen;
each of $R^1$ and $R^2$ is independently hydrogen, halogen, cyano, unsubstituted or halogenated $C_{1-8}$alkyl, or the aryl group

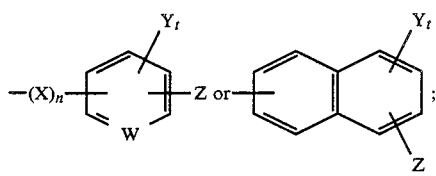

provided that when one of $R^1$ or $R^2$ is an aryl group, the other of $R^1$ or $R^2$ is not an aryl group;
$R^3$ is hydrogen or halogen;
n is zero or one;
t is one, two, three or four;
W is nitrogen or CH;
X is oxygen, sulfur or methylene;
Y is hydrogen, halogen or unsubstituted or halogenated $C_{1-8}$alkyl; and
Z is halogen, or unsubstituted or halogenated $C_{1-8}$alkyl, unsubstituted or halogenated $C_{1-8}$alkoxy, or unsubstituted or halogenated phenoxy;
and the agriculturally acceptable salts or metal complexes thereof.

2. A compound according to claim 1 wherein $X^1$ is chloro or fluoro; $X^2$ is hydrogen or fluoro; $X^3$ is hydrogen; each of $R^1$ and $R^2$ is independently hydrogen, halogen, unsubstituted or halogenated $C_{1-4}$alkyl or the group

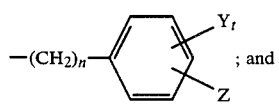 ; and $R^3$ is hydrogen.

3. A compound according to claim 2 of the following formula

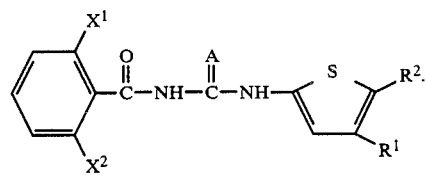

4. A compound according to claim 3 wherein A is oxygen and $R^2$ is chloro or the group

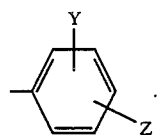

5. A compound according to claim 4 wherein Y is hydrogen, fluoro or chloro and Z is chloro, bromo, fluoro methyl, trifluoromethyl, methoxy, difluoromethoxy or trifluoromethoxy.

6. A compound according to claim 5 wherein $R^1$ is hydrogen, chloro, methyl or trifluoromethyl.

7. A compound according to claim 6 of the following formula:

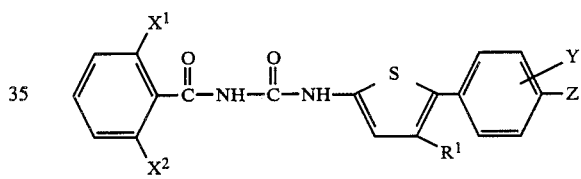

8. A compound according to claim 7 wherein $X^1$ is chloro and $X^2$ is hydrogen.

9. The compound N-2-chlorobenzoyl-N'-[5-(4-trifluoromethylphenyl)-4-methyl-2-thienyl]urea, according to claim 8.

10. A compound according to claim 7 wherein each of $X^1$ and $X^2$ is fluoro.

11. The compound N-2,6-difluorobenzoyl-N'-[5-(4-chlorophenyl)-4-methyl-2-thienyl]urea, according to claim 10.

12. The compound N-2,6-difluorobenzoyl-N'-[4-methyl-5-(4-trifluoromethylphenyl)-2-thienyl]urea, according to claim 10.

13. The compound N-2,6-difluorobenzoyl-N'-[4-methyl-5-(4-bromophenyl)-2-thienyl]urea, according to claim 10.

14. The compound N-2,6-difluororbenzoyl-N'-[5-(4-chlorophenyl)-4-trifluoromethyl-2-thienyl]urea, according to claim 10.

15. The compound N-2,6-difluorobenzoyl-N'-[5-(2-chloro4-trifluoromethoxyphenyl)-4-methyl-2-thienyl]urea, according to claim 10.

16. The compound N-2,6-difluorobenzoyl-N'-[4-methyl-5-(2,4-dichlorophenyl)-2-thienyl]urea, according to claim 10.

17. A compound according to claim 2 of the following formula:

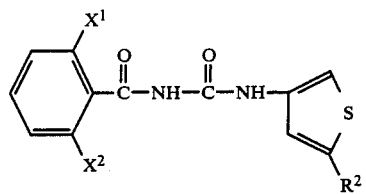

wherein $R^2$ is methyl or trifluoromethyl.

18. A method for the control of pests which comprises applying to the pest or its locus a pest controlling amount of a compound of formula A as defined in claim 1.

19. A compound according to claim 1 wherein A represents oxygen.

20. A compound according to claim 1 wherein when $R_3$ is hydrogen, $R_1$ and $R_2$ are both methyl and the urea radical is attached to the 2-position of the thienyl radical, then A represents oxygen.